US00PP31233P2

(12) United States Plant Patent

Pakozdi et al.

(10) Patent No.: US PP31,233 P2

(45) Date of Patent: Dec. 17, 2019

(54) STRAWBERRY PLANT VARIETY NAMED 'DRISSTRAWFIFTYNINE'

(50) Latin Name: ***Fragaria* x *ananassa***
Varietal Denomination: DrisStrawFiftyNine

(71) Applicant: Driscoll's, Inc., Watsonville, CA (US)

(72) Inventors: Katalin Monika Pakozdi, Maidstone (GB); Carlos D. Fear, Aptos, CA (US); Alessandra Lillo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/998,015

(22) Filed: Jun. 11, 2018

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209, 208
CPC ..... A01H 5/08; A01H 5/0893; A01H 5/0831; A01H 6/74; A01H 6/7409
See application file for complete search history.

(56) References Cited

U.S. PATENT DOCUMENTS

PP1,756 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.

(Continued)

OTHER PUBLICATIONS

The Fruit Grower 2017 Fruit Focus 2017 Berry Gardens expands market share, retrieved on May 13, 2017, retrieved from the Internet at http://www.hortnews.com/publications/fruitgrower/august/2017/files/assets/common/downloads/Fru%20AUG%2017.pdf, cover page and pp. 10-11. (Year: 2017).*

Upov Pluto Plt Variety Database 20190513, retrieved on May 13, 2019, retrieved from the Internet at https://www3.wipo.int/pluto/user/en/index.jsp, one page. (Year: 2019).*

"An Early Season with Many Highs", Berry Gardens 2017, Online at https://www.berrygardens.co.uk/an-early-season-with-many-highs/, 6 pp. (Year: 2017).*

(Continued)

*Primary Examiner* — June Hwu

(74) *Attorney, Agent, or Firm* — Morrison & Foerster LLP

(57) ABSTRACT

A new and distinct variety of strawberry plant named 'DrisStrawFiftyNine', particularly characterized by its yield potential, fruit with less seed, fruit size, fruit appearance, and fruit shelf-life, is disclosed.

2 Drawing Sheets

(56) References Cited

U.S. PATENT DOCUMENTS

| | | | |
|---|---|---|---|
| PP20,248 | P3 | 9/2009 | Rogers et al. |
| PP20,363 | P2 | 9/2009 | Chandler |
| PP20,701 | P2 | 2/2010 | Gilford et al. |
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 * | 10/2018 | Stewart ..... Plt./208 |
| PP29,729 | P2 * | 10/2018 | Kibbe ..... Plt./208 |
| PP29,730 | P2 * | 10/2018 | Kibbe ..... Plt./208 |
| PP29,731 | P2 * | 10/2018 | Ferguson ..... Plt./209 |
| PP29,747 | P2 * | 10/2018 | Vitten ..... Plt./208 |
| PP29,748 | P2 * | 10/2018 | Vitten ..... Plt./208 |
| PP29,749 | P2 * | 10/2018 | Stewart ..... Plt./209 |
| 2003/0079263 | P1 | 4/2003 | Gilford et al. |
| 2013/0276182 | P1 | 10/2013 | Fear et al. |

OTHER PUBLICATIONS

"An Early Season With Many Highs", Berry Gardens, Available Online at <https://www.berrygardens.co.uk/an-early-season-with-many-highs/>, Aug. 21, 2017, 6 pages.

Katie, "My Green Pod", Available online at <https://www.mygreenpod.com/articles/its-strawberry-time/>, May 30, 2017, 3 pages.

Fear, et at, Unpublished U.S. Appl. No. 15/998,014, filed Jun. 11, 2018, titled "Strawberry Plant Variety Named 'DrisStrawFiftyEight'".

Ferguson et al., Unpublished U.S. Appl. No. 15/731,546, filed Jun. 26, 2017, titled "Strawberry Plant Variety Named 'DrisStrawFiftySix'".

Kibbe et al., Unpublished U.S. Appl. No. 15/731,542, filed Jun. 26, 2017, titled "Strawberry Plant Variety Named 'DrisStrawFiftyTwo'".

Kibbe et al., Unpublished U.S. Appl. No. 15/731,545, filed Jun. 26, 2017, titled "Strawberry Plant Variety Named 'DrisStrawFiftyOne'".

Mendoza et al., Unpublished U.S. Appl. No. 15/998,020, filed Jun. 12, 2018, titled "Strawberry Plant Variety Named 'DrisStrawSixtyOne'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl. No. 15/731,415, filed Jun. 6, 2017, titled "Strawberry Plant Variety Named 'DrisStrawFiftyThree'".

Stewart et al., Unpublished U.S. Appl. No. 15/731,421, filed Jun. 6, 2017, titled "Strawberry Plant Variety Named 'DrisStrawFiftySeven'".

Stewart et al., Unpublished U.S. Appl. No. 15/998,031, filed Jun. 14, 2018, titled "Strawberry Plant Variety Named 'DrisStrawSixtyFour'".

Vitten et al., Unpublished U.S. Appl. No. 15/731,559, filed Jun. 27, 2017, titled "Strawberry Plant Variety Named 'DrisStrawFiftyFour'".

Vitten et al., Unpublished U.S. Appl. No. 15/731,560, filed Jun. 27, 2017, titled "Strawberry Plant Variety Named 'DrisStrawFiftyFive'".

* cited by examiner

STRAWBERRY PLANT VARIETY NAMED 'DRISSTRAWFIFTYNINE'

Botanical classification: *Fragaria* x *ananassa.*

Varietal denomination: The varietal denomination of the claimed variety of strawberry plant is 'DrisStrawFiftyNine'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawFiftyNine'.

Strawberry plant variety 'DrisStrawFiftyNine' was discovered in East Malling, Kent County, the United Kingdom in August of 2012, and originated from a cross between the proprietary female parent 'UUKE 116-003' (unpatented) and the proprietary male parent 'UUKE 167-027' (unpatented). A single plant was selected and asexually propagated via stolons in the Netherlands in August of 2012.

'DrisStrawFiftyNine' was subsequently asexually propagated via stolons, and underwent further testing at a farm in East Malling, Kent County, the United Kingdom for five years (2012 to 2016). The present variety has been found to be stable and reproduce true to type through successive asexual propagations via stolons.

'DrisStrawFiftyNine' exhibits the following distinguishing characteristics when grown under normal horticultural practices in East Malling, Kent County, the United Kingdom:

1. High yield; and
2. Fruit having less seed, better appearance, and improved shelf-life.

'DrisStrawFiftyNine' was selected for its yield potential, fruit with less seed, fruit size, fruit appearance, and fruit shelf-life.

DESCRIPTION OF THE DRAWINGS

This new strawberry plant is illustrated by the accompanying photographs which show fruit and leaves of the plant. The colors shown are as true as can be reasonably obtained by conventional photographic procedures. The photographs are of plants that are six months old.

DESCRIPTION OF THE NEW VARIETY

Figure 1:
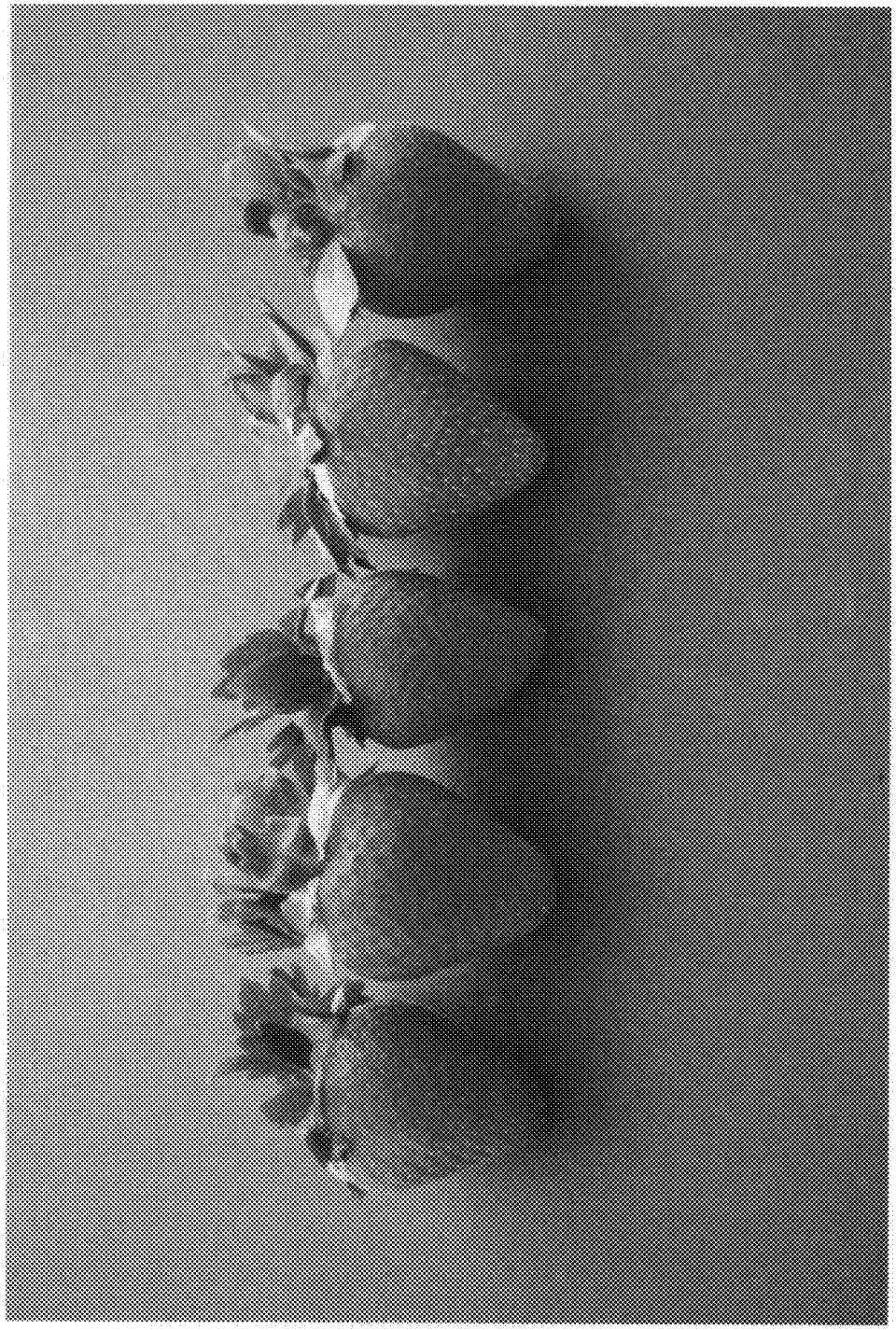
FIG. 1 illustrates whole fruit of variety 'DrisStrawFiftyNine'.
Figures 2A, 2B:
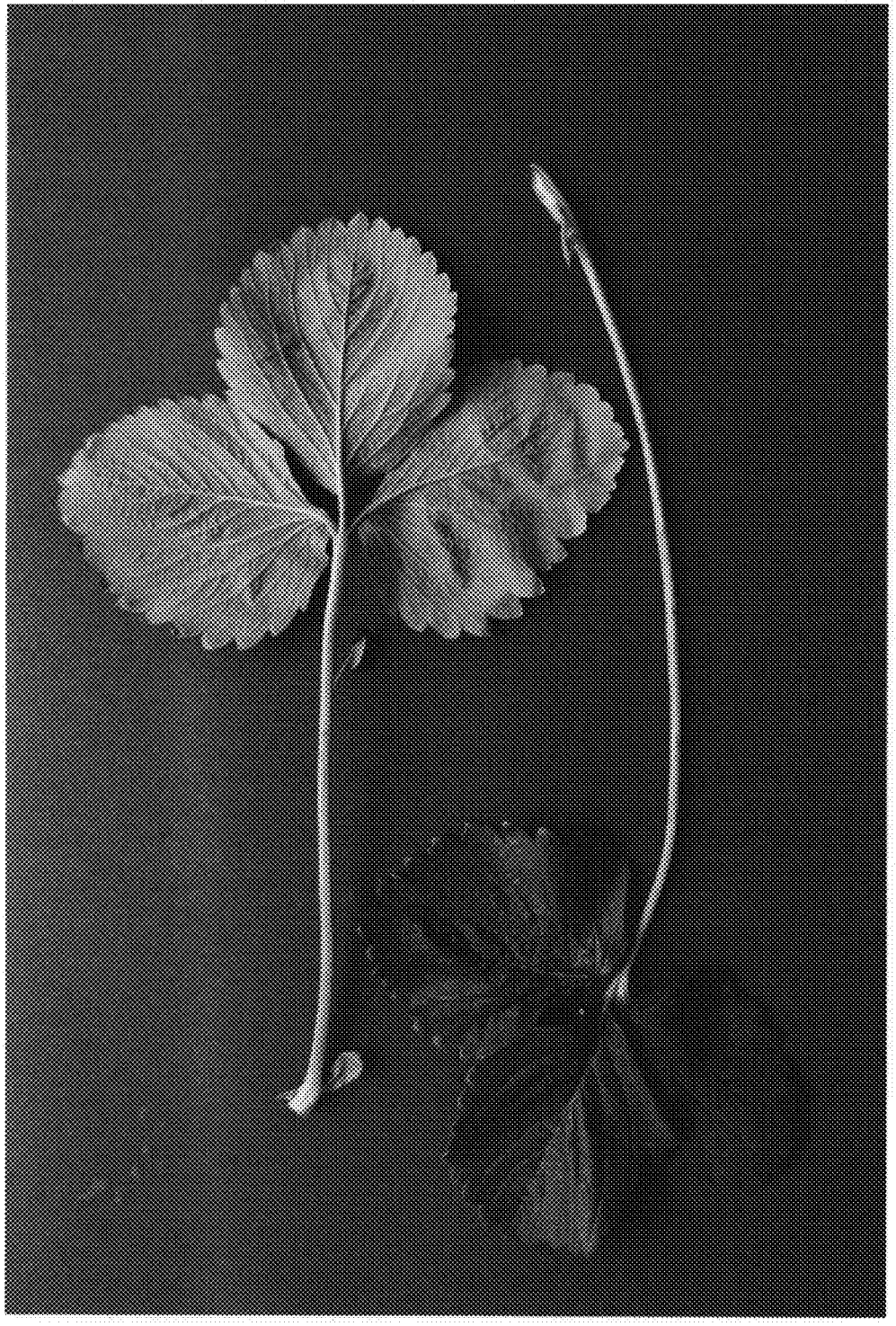
FIG. 2A illustrates the upper surface of a leaf of variety 'DrisStrawFiftyNine'.
FIG. 2B illustrates the lower surface of a leaf of variety 'DrisStrawFiftyNine'.

The following detailed descriptions set forth the distinctive characteristics of 'DrisStrawFiftyNine'. The data which define these characteristics is based on observations taken in East Malling, Kent County, the United Kingdom from 2012 to 2016. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFiftyNine' has not been observed under all possible environmental conditions. The botanical description of 'DrisStrawFiftyNine' was taken from plants that were six months old. The indicated values represent averages calculated from measurements of several plants. Color references are primarily to The RHS Colour Chart of The Royal Horticultural Society of London (RHS) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawFiftyNine'.

Parentage:

*Female parent.*—The proprietary variety 'UUKE 116-003' (unpatented).

*Male parent.*—The proprietary variety 'UUKE 167-027' (unpatented),

Plant:

*Height.*—39.7 cm.

*Diameter.*—45.0 cm.

*Number of crowns/plant.*—5.

*Growth habit.*—Semi-upright.

Stolon:

*Average number of daughter plants per square foot.*—44.

*Diameter at bract.*—4.794 mm.

*Anthocyanin coloration.*—Absent to medium.

*Average length.*—47.8 cm.

*Surface texture.*—Glabrous.

*Color.*—RHS 145A (Strong yellow-green).

Leaf:

*Number of leaflets.*—Three only.

*Color of upper surface.*—RHS NN137B (Greyish olive green).

*Color of lower surface.*—RHS NN137D (Greyish olive green).

*Leaf length.*—37.5 cm.

*Leaf width.*—19 cm.

*Blistering.*—Absent or weak.

*Glossiness.*—Medium.

*Variegation.*—Absent.

*Terminal leaflets.*—Length: 10.9 cm. Width: 9.1 cm. Length/width ratio: 1.2. Number of teeth/terminal leaflet: 26. Shape of base: Obtuse. Margin: Crenate. Shape in cross section: Concave.

*Petiole.*—Length: 26.0 cm. Diameter: 6.08 mm. Attitude of hairs: Horizontal. Bract frequency (number present on each petiole): 1. Petiole color: RHS 145A (Strong yellow-green).

*Petiolule.*—Length: 11.12 mm. Diameter: 2.78 mm. Petiolule color: RHS 145B (Light yellow-green).

*Stipule.*—Length: 3.9 cm. Width: 8.68 mm. Stipule color: RHS N144D (Strong yellow-green). Anthocyanin coloration: Absent.

Inflorescence:

*Position in relation to foliage.*—Above.

*Pedicel.*—Attitude of hairs: Upwards.

*Flower.*—Flower diameter (petal tip to petal tip on non-flattened flower): 34.46 mm. Arrangement of petals: Overlapping. Stamen: Present. Typical and observed number of flowers per plant: 28.

*Petal.*—Length: 13.37 mm. Width: 16.14 mm. Length/width ratio: 0.8. Typical and observed petal number: 6. Color of upper side: RHS NN155C (White). Color of lower side: RHS NN155C (White). Apex shape: Rounded. Base shape: Obtuse.

*Calyx.*—Diameter (sepal tip to sepal tip, measured on back of flower): 44.49 mm. Size of calyx in relation to corolla: Larger.

*Sepal.*—Length (sepal tip to point of attachment to receptacle): 17.42 mm. Width: 10.40 mm. Typical and observed sepal number: 6. Sepal color: RHS N134A (Dark yellowish green). Apex shape: Truncate/emarginate. Base shape: Orbicular.

Fruit:

*Length.*—48.69 mm.

*Width.*—40.62 mm.

*Length/width ratio.*—1.2.

*Fruit hollow length.*—26.30 mm.

*Fruit hollow width.*—16.38 mm.

*Fruit hollow length/width ratio.*—1.6.

*Shape.*—Conical.

*Color.*—RHS 44A (Vivid red).

*Position of achenes.*—Level with surface.

*Position of calyx attachment.*—Level with fruit.

*Diameter of calyx in relation to diameter of fruit.*—Much larger.

*Attitude of sepals.*—Upwards.

*Color of flesh (excluding core).*—RHS 40B (Vivid reddish orange).

*Color of core.*—RHS 41C (Moderate reddish orange).

*Evenness of color.*—Even or very slightly uneven.

*Glossiness.*—Medium.

*Evenness of surface.*—Even or very slightly uneven.

*Width of band without achenes.*—Absent or very narrow.

*Firmness.*—Medium.

*Cavity.*—Absent or small.

*Brix percentage.*—9.1%.

*Average number of achenes per fruit.*—322.

*Fruit market use.*—Fresh consumption.

*Fruit shelf life.*—longer shelf life as compared to fruit of female parent 'UUKE 116-003 '.

*Fruiting truss.*—Length: 35.7 cm. Diameter: 5.66 mm. Number of berry per fruiting truss: 9.

Production:

*Flowering interval.*—May to September.

*Harvest interval.*—Mid-May to early September.

*Type of bearing.*—Fully remontant.

*Productivity.*—1.023 kg to 1.050 kg of fruit per season from two-month-old to six-month-old plants when grown in East Malling, Kent County, the United Kingdom.

Resistance to diseases:

*Powdery mildew (Podosphaera macularis).*—Moderately resistant.

*Verticillium wilt.*—Moderately susceptible.

COMPARISON WITH PARENTAL AND COMMERCIAL VARIETIES

'DrisStrawFiftyNine' differs from the proprietary female parent 'UUKE 116-003' (unpatented) in that plants of 'DrisStrawFiftyNine' produce higher yields of fruit as compared to plants of 'UUKE 116-003'. Additionally, fruit of 'DrisStrawFiftyNine' are less seedy, larger in size, better in appearance, and have a longer shelf-life as compared to fruit of 'UUKE 116-003'.

'DrisStrawFiftyNine' differs from the proprietary male parent 'UUKE 167-027' (unpatented) in that plants of 'DrisStrawFiftyNine' produce higher yields of fruit as compared to plants of 'UUKE 167-027'. Additionally, fruit of 'DrisStrawFiftyNine' are smaller in size as compared to fruit of "UUKE 167-027'.

'DrisStrawFiftyNine' differs from the commercial variety 'DrisStrawThirtyFive' (U.S. Plant Pat. No. 24,745) in that plants of 'DrisStrawFiftyNine' have an upright growth habit, while plants of 'DrisStrawThirtyFive' have a semi-upright growth habit. Additionally, plants of 'DrisStrawFiftyNine' have medium vigor, while plants of 'DrisStrawThirtyFive' have strong vigor. Moreover, the type of bearing of 'DrisStrawFiftyNine' is fully remontant, while the type of bearing of 'DrisStrawThirtyFive' is not remontant.

'DrisStrawFiftyNine' differs from the commercial variety 'DrisStrawTwo' (U.S. Plant Pat. No. 18,878) in that terminal leaflets of 'DrisStrawFiftyNine' have an obtuse shape of base, while terminal leaflets of 'DrisStrawTwo' have a rounded shape of base. Additionally, fruit of 'DrisStrawFiftyNine' have absent or a very narrow width of band without achenes, while fruit of 'DrisStrawTwo' have a medium width of band without achenes. Moreover, fruit of 'DrisStrawFiftyNine' have a calyx attachment that is level with fruit, while fruit of 'DrisStrawTwo' have a calyx attachment that is raised from fruit.

We claim:

1. A new and distinct variety of strawberry plant named 'DrisStrawFiftyNine' as shown and described herein.

* * * * *